United States Patent
Shimamoto

(10) Patent No.: US 9,612,435 B2
(45) Date of Patent: Apr. 4, 2017

(54) OPTICAL SCANNING DEVICE, AND ENDOSCOPE, MICROSCOPE, AND PROJECTOR EACH PROVIDED WITH THE SAME

(71) Applicant: OLYMPUS CORPORATION, Tokyo (JP)

(72) Inventor: Atsuyoshi Shimamoto, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 140 days.

(21) Appl. No.: 14/193,439

(22) Filed: Feb. 28, 2014

(65) Prior Publication Data

US 2014/0177021 A1    Jun. 26, 2014

Related U.S. Application Data

(63) Continuation of application No. PCT/JP2012/071821, filed on Aug. 29, 2012.

(30) Foreign Application Priority Data

Sep. 2, 2011    (JP) .................. 2011-191820

(51) Int. Cl.
*G02B 26/08* (2006.01)
*G02B 26/10* (2006.01)
(Continued)

(52) U.S. Cl.
CPC ........ *G02B 26/101* (2013.01); *A61B 1/00165* (2013.01); *A61B 1/00172* (2013.01); *G02B 21/0044* (2013.01); *G02B 23/2423* (2013.01); *G02B 26/103* (2013.01); *F04C 2270/041* (2013.01)

(58) Field of Classification Search
CPC ............ G02B 21/0044; G02B 23/2423; G02B 26/103; G02B 26/101; A61B 1/00165; A61B 1/00172
USPC ....... 385/25; 359/198.1–199.4, 200.6–200.8, 359/224.1–224.2
See application file for complete search history.

(56) References Cited

U.S. PATENT DOCUMENTS 6,294,775 B1    9/2001  Seibel et al.
7,920,312 B2 *  4/2011  Rosman ............... A61B 5/0062
                                                  359/199.1

FOREIGN PATENT DOCUMENTS

JP    2008-116922 A    5/2008
JP    2012-040177 A    3/2012
(Continued)

OTHER PUBLICATIONS

Extended Supplementary European Search Report dated May 7, 2015 from related European Application No. 12 82 6786.1.
(Continued)

*Primary Examiner* — James Phan
(74) *Attorney, Agent, or Firm* — Scully, Scott, Murphy & Presser, P.C.

(57) ABSTRACT

An optical scanning device includes an optical fiber, a holding member cantilevering the optical fiber, a first driving device placed on the distal end of the optical fiber and making the optical fiber vibrate in a first direction, and a second driving device placed between the holding member for the optical fiber and the first driving device and making the optical fiber vibrate in a second direction which crosses the first direction.

15 Claims, 4 Drawing Sheets

(51) Int. Cl.
G02B 21/00 (2006.01)
G02B 23/24 (2006.01)
A61B 1/00 (2006.01)

(56) References Cited

FOREIGN PATENT DOCUMENTS

| JP | 2012-042721 A | 3/2012 |
| WO | 95/25971 A2 | 9/1995 |
| WO | WO 2006/032106 A1 | 3/2006 |

OTHER PUBLICATIONS

Wang, W. et al., Two-dimensional mechanically resonating fiber optic scanning display system, Optical Engineering, (Sep. 2010), vol. 49, No. 9, pp. 097401-1-097401-8.
International Search Report issued in PCT/JP2012/071821 dated Oct. 2, 2012.

\* cited by examiner

DRIVE SIGNAL FOR VERTICAL ACTUATOR + DRIVE SIGNAL FOR HORIZONTAL ACTUATOR = SPIRAL SCAN PATTERN

VERTICAL DIRECTION (LOW-SPEED) + HORIZONTAL DIRECTION (HIGH-SPEED) = RASTER PATTERN

OPTICAL SCANNING DEVICE, AND ENDOSCOPE, MICROSCOPE, AND PROJECTOR EACH PROVIDED WITH THE SAME

This application claims benefits of Japanese Application No. 2011-191820 filed in Japan on Sep. 2, 2011, the contents of which are incorporated herein by reference.

BACKGROUND OF THE INVENTION

1. Field of the Invention

This invention relates to a method of actuating optical fibers for optical scanning devices used for optical scanning endoscopes, optical scanning microscopes, optical scanning projectors, or the like in which an optical fiber vibration scanning is used.

2. Description of Related Art

Endoscopes in which scanning is performed by an optical fiber includes an endoscope disclosed in Japanese Patent TOKUHYOU No. 2010-527028. In the endoscope disclosed in Japanese Patent TOKUHYOU No. 2010-527028, piezoelectric devices B are put on the base of an optical fiber A in two directions as shown in FIG. 5 and produce resonant vibration in the X- and Y-directions, so that a beam of light is scanned. And, resonant vibration is used for scanning in the endoscope disclosed in Japanese Patent TOKUHYOU No. 2010-527028, so that drive frequencies in the X- and Y-directions become approximately equal to each other and its scan pattern becomes spiral as shown in FIG. 7. Also, in this scanning for which resonant vibration is used, modulation is performed by increasing or decreasing amplitude gradually, so that driving signals are complicated. Also, the center of the spiral scan pattern is widely different from the periphery of the spiral scan pattern in scanning speed.

On the other hand, it is possible to scan a beam of light with a raster pattern as shown in FIG. 8 by making drive frequencies in the X- and Y-directions widely differ from each other to synchronize the drive frequencies in the X- and Y-directions. This scanning does not require amplitude modulation, drive signals become simple, and it is possible scan a beam of light on a rectangular region, so that an image conversion can be performed without waste. Also, the scanning pitch in the vicinity of the center of the scan pattern is uniform, the vicinity of the center of the scan pattern becoming an object to be observed mainly. As a result, exposure time for an object to be imaged is uniform.

Also, endoscopes in which a scanning by an optical fiber is performed using electromagnetic drive include an endoscope disclosed in Japanese Patent TOKUKAI No. 2008-116922. In the endoscopes disclosed in Japanese Patent TOKUKAI No. 2008-116922, magnets C1 and C2 are fitted to an optical fiber A as shown in FIG. 6, electromagnetic coils D are arranged around the magnets C1 and C2, and the optical fiber A is driven using electromagnetic force. And, a non-resonant scanning by the optical fiber A is performed at low speed in the Y-direction and a scanning by the optical fiber A is performed at a second-order resonant frequency in the X-direction so that the scanning is performed with a raster pattern that is shown in FIG. 8.

SUMMARY OF THE INVENTION

An optical scanning device according to the present invention includes: an optical fiber; a holding member cantilevering the optical fiber; a first driving device placed on a distal end of the optical fiber and making the optical fiber vibrate in a first direction; and a second driving device placed between the holding member for the optical fiber and the first driving device and making the optical fiber vibrate in a second direction which crosses the first direction.

Also, a method of driving an optical fiber provided for an optical scanning device and cantilevered by a holding member, according to the present invention, includes: making the optical fiber vibrate in a first direction by a first driving device placed on a distal end of the optical fiber; and making the optical fiber vibrate in a second direction by a second driving device placed between the holding member for the optical fiber and the first driving device, the second direction crossing the first direction.

The features and advantages of the present invention will become apparent from the following detailed description of the embodiments when taken in conjunction with the accompanying drawings.

DETAILED DESCRIPTION OF THE PREFERRED EMBODIMENTS

Embodiment 1

Figure 1A:
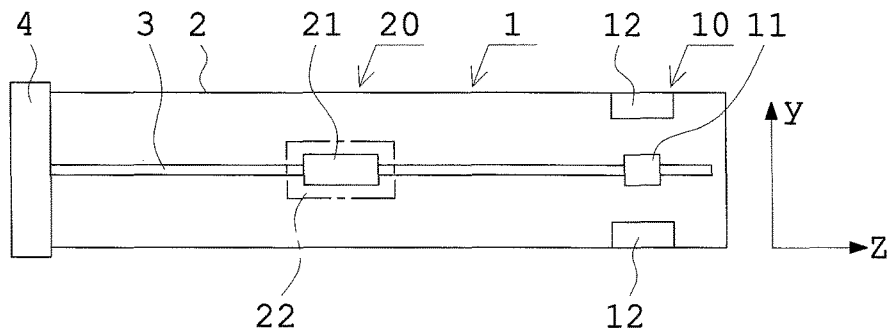
FIG. 1A is an explanatory view showing an optical scanning device according to one embodiment of the present invention and is a side view showing the optical scanning device when viewed in the Y-direction.
Figure 1B:
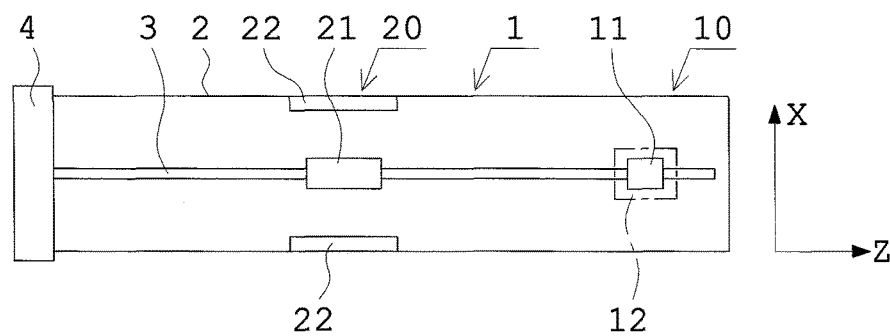
FIG. 1B is an explanatory view showing the optical scanning device according to the one embodiment of the present invention and is a side view showing the optical scanning device when viewed in the X-direction.

Next, an example in which magnetic force is used for first and second driving devices is explained as one embodiment of optical scanning devices according to the present invention on the basis of FIGS. 1A and 1B.

An optical scanning device 1 includes: a housing 2 basically having a cylindrical shape; an optical fiber 3 arranged in the housing 2; and first and second driving devices 10 and 20. A holding member 4 for supporting the optical fiber 3 is provided on the one end of the cylindrical housing 2. And, the optical fiber 3 is supported in the center of the holding member 4 with one end of the optical fiber 3 becoming a fixed end.

The first driving device 10 is arranged on the front end side of the optical fiber 3, the front end of the optical fiber 3 becoming a free end opposite to the holding member 4. The first driving device 10 is composed of: a permanent magnet 11 arranged on the outer circumference of the optical fiber 3; and an electromagnetic coil 12 arranged on the inner circumference of the housing 2. Also, a control device for controlling the first driving device 10 is arranged at a proper place, the control device being not shown in the drawings. Besides, although the permanent magnet 11 is arranged on the optical fiber 3 and the electromagnetic coil 12 is arranged on the housing 2 in the example shown in FIGS. 1A and 1B, a combination of the permanent magnet 11 and the electromagnetic coil 12 in the first driving device 10 is not limited to the example shown in FIGS. 1A and 1B.

Also, the second driving device 20 is arranged between the first driving device 10 and the holding member 4. The second driving device 20 is composed of: a permanent magnet 21 arranged on the outer circumference of the optical fiber 3; and an electromagnetic coil 22 arranged on the inner circumference of the housing 2. Also, a control device for controlling the second driving device 20 is arranged at a proper place, the control device being not shown in the drawings. Besides, although the permanent magnet 21 is arranged on the optical fiber 3 and the electromagnetic coil 22 is arranged on the housing 2 in the example shown in FIGS. 1A and 1B, a combination of the permanent magnet 21 and the electromagnetic coil 22 in the second driving device 20 is not limited to the example shown in FIGS. 1A and 1B.

And, the optical fiber 3 is a single mode fiber, is vibrated in the Y-direction by the first driving device 10, and is vibrated in the X-direction by the second driving device 20. Besides, the permanent magnets 11 and 21 may be replaced with magnetic substances. Also, the permanent magnets 11 and 21 may be shaped like a cylinder or a rectangular, hexagonal, or octagonal pillar. Anyway, the optical fiber 3 has only to be vibrated in the Y- and X-directions by magnetic force.

Besides, the present invention does not necessarily require that the first direction in which the optical fiber 3 is vibrated directly by the first driving device 10 should be perpendicular to the second direction in which the optical fiber 3 is vibrated directly by the second driving device 20. In the present invention, the first direction has only to cross the second direction. And, the directions in which the optical fiber 3 is vibrated by the first driving device 10 and the second driving device 20 respectively have only to be consequently divided into vibrations in the X- and Y-directions that are perpendicular to each other.

In order that a low-speed scanning in the Y-direction can be performed by the first driving device 10 that is arranged on the front-end side of the optical fiber 3, the optical fiber 3 is configured to be vibrated at a first-order resonant frequency in the Y-direction with the optical fiber 3 resonating or to be vibrated at a frequency lower than the first-order resonant frequency in the Y-direction without being made to resonate. And, in order to achieve such an operation, the permanent magnet 11 is arranged to be located nearer to the front end of the optical fiber 3 than the node nearest to the front end of the optical fiber 3 is located in the vibration of the optical fiber 3.

Also, in order that a high-speed scanning in the X-direction can be performed by the second driving device 20 that is arranged between the holding member 4 for the optical fiber 3 and the first driving device 10, the optical fiber 3 is configured to be vibrated in the X-direction at a second-order resonant frequency or at a high-order resonant frequency higher than the second-order resonant frequency with the optical fiber 3 resonating. And, in order to achieve such an operation, the permanent magnet 21 is arranged at a position of a node or anti-node in the vibration of the optical fiber 3. However, there is no necessity that the position of the permanent magnet 21 arranged should exactly correspond with the position of the node or anti-node in the vibration of the optical fiber 3. Also, a plurality of second driving devices 20 may be also placed at a plurality of places between the holding member 4 for the optical fiber 3 and the first driving device 10 respectively in accordance with orders of resonant vibrations of the optical fiber 3.

According to the optical scanning device of the embodiment 1, the first driving device 10 is arranged on the distal end of the optical fiber 3, so that the bending moment on the optical fiber 3 becomes large. As a result, a first-order resonant frequency becomes low, so that it is possible to increase amplitude efficiently when the optical fiber is vibrated without being made to resonate. For example, when the first direction is the Y-direction, a scanning in the Y-direction by the optical fiber 3 can be performed at low speed.

On the other hand, the second driving device 20 is arranged between the holding member 4 for the optical fiber 3 and the first driving device 10, so that the optical fiber 3 can be vibrated to resonate at a high order resonant frequency. When the second direction is the X-direction for example, a scanning in the X-direction by the optical fiber 3 can be performed at high speed.

Also, in the optical scanning device of the present embodiment, when the first direction in which the optical fiber 3 is made to vibrate by the first driving device 10 is perpendicular to the second direction which crosses the first direction and in which the optical fiber 3 is made to vibrate by the second driving device 20, the optical fiber 3 is vibrated by the first driving device 10 vibrating the optical fiber 3 in the first direction and by the second driving device 20 vibrating the optical fiber 3 in the second direction perpendicular to the first direction with the X-direction perpendicular to the Y-direction, so that the raster scan can be performed.

Also, in the optical scanning device of the present embodiment, when a vibration frequency at which the optical fiber 3 is made to vibrate in the first direction by the first driving device 10 is lower than a vibration frequency at which the optical fiber 3 is made to vibrate in the second direction by the second driving device 20, the raster scan can be easily performed by making a vibration frequency for vibrating the optical fiber 3 in the Y-direction by the first driving device 10 lower than a vibration frequency for vibrating the optical fiber 3 in the X-direction by the second driving device 20, because the first direction and the second direction are perpendicular to each other.

Also, in the optical scanning device of the present embodiment, in the case where the first driving device 10 vibrates the optical fiber 3 with the optical fiber 3 resonating, a bending moment on the optical fiber 3 becomes large because the first driving device 10 is arranged on the front-end side of the optical fiber 3. As a result, the first-order resonant frequency can be lowered, and a low-speed scanning can be performed by vibrating the optical fiber 3 in the Y-direction at the first-order resonant frequency.

Also, in the optical scanning device of the present embodiment, in the case where the first driving device 10 vibrates the optical fiber 3 without making the optical fiber 3 resonate, a bending moment on the optical fiber 3 becomes large because the first driving device 10 is arranged on the front-end side of the optical fiber 3. As a result, the first-order resonant frequency can be lowered, and a desired low-speed scanning can be performed by vibrating the optical fiber 3 in the Y-direction at a frequency lower than the first-order resonant frequency without making the optical fiber 3 resonate.

Also, in an optical scanning device according to the present invention, in the case where the second driving device 20 vibrates the optical fiber 3 with the optical fiber 3 resonating, the optical fiber 3 can be made to vibrate with the optical fiber 3 resonating at a high order, because the second driving device 20 is arranged between the holding member 4 for the optical fiber 3 and the first driving device 10. As a result, any high-order resonant frequency can be used, and a desired high-speed scanning can be performed by vibrating the optical fiber 3 in the X-direction at a high frequency with the optical fiber 3 resonating.

Also, in the optical scanning device of the present embodiment, when the first driving device 10 or the second driving device 20 is composed of: a magnet or magnetic substance; and an electromagnetic coil, it is sufficient to merely place a magnet or magnetic substance on the optical-fiber-3 side, so that the structure of the optical fiber 3 can be simplified.

Embodiment 2

Figure 2A:
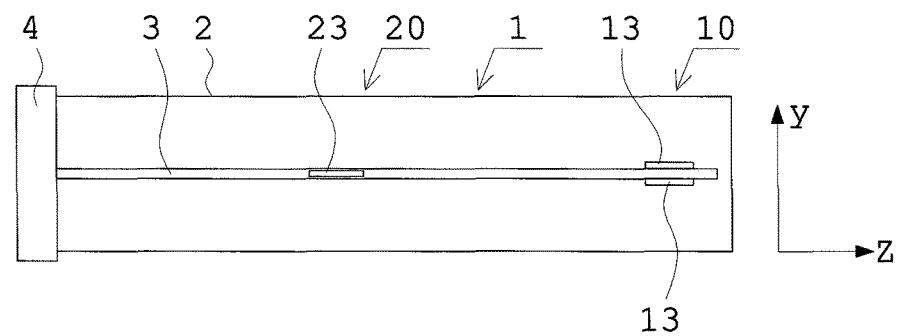
FIG. 2A is an explanatory view showing an optical scanning device according to another embodiment of the present invention and is a side view showing the optical scanning device when viewed in the Y-direction.
Figure 2B:
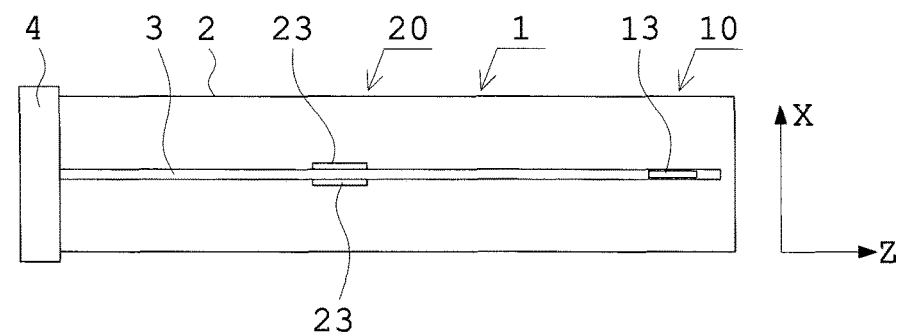
FIG. 2B is an explanatory view showing the optical scanning device according to another embodiment of the present invention and is a side view showing the optical scanning device when viewed in the X-direction.

Next, an embodiment 2 in which thin film-shaped piezoelectric devices are used for first and second driving devices is explained as another embodiment of optical scanning devices according to the present invention on the basis of FIGS. 2A and 2B. Because an optical scanning device of the embodiment 2 basically has the same structure as the optical scanning device of the above-described embodiment 1 does, only characteristics in which the optical scanning devices of the embodiment 2 differs from the optical scanning devices of the embodiment 1 are explained.

In the optical scanning device of the embodiment 2, thin film-shaped piezoelectric devices 13 constituting the first driving device 10 are put on the circumference of the optical fiber 3 with the piezoelectric devices 13 opposite to each other so that the piezoelectric devices 13 vibrate the optical fiber 3 in the Y-direction.

Also, thin film-shaped piezoelectric devices 23 constituting the second driving device 20 are put on the circumference of the optical fiber 3 with the piezoelectric devices 23 opposite to each other so that the piezoelectric devices 23 vibrate the optical fiber 3 in the X-direction.

In order that a low-speed scanning in the Y-direction can be performed by the first driving device 10 that is arranged on the front-end side of the optical fiber 3, the optical fiber 3 is configured to be vibrated at a first-order resonant frequency in the Y-direction with the optical fiber 3 resonating or to be vibrated at a frequency lower than the first-order resonant frequency in the Y-direction without being made to resonate. And, in order to achieve such an operation, the piezoelectric devices 13 are arranged to be located nearer to the front end of the optical fiber 3 than the node nearest to the front end of the optical fiber 3 is located in the vibration of the optical fiber 3.

Also, in order that high-speed scanning in the X-direction can be performed by the second driving device 20 which is placed between the holding member 4 for the optical fiber 3 and the first driving device 10, the optical fiber 3 is configured to be vibrated in the X-direction at a second-order resonant frequency or at a high-order resonant frequency higher than the second-order resonant frequency with the optical fiber 3 resonating. And, in order to achieve such an operation, the piezoelectric devices 23 are placed at a position of a node or antinode in the vibration of the optical fiber 3. However, there is no necessity that the position at which the piezoelectric devices 23 are placed should exactly correspond with the position of the node or antinode in the vibration of the optical fiber 3 respectively. Also, a plurality of second driving devices 20 may be also placed at a plurality of places between the holding member 4 for the optical fiber 3 and the first driving device 10 respectively.

According to the optical scanning device of the present embodiment, the first driving device 10 or the second driving device 20 is composed of a piezoelectric device that is formed into a thin film and that is provided for the optical fiber 3, so that the piezoelectric device has only to be provided for the optical fiber 3. As a result, the electromagnetic coil or the like is unnecessary and the structure of the optical scanning device can be simplified.

Embodiment 3

Next, a method of carrying out a raster scan or a Lissajous scan with the above described optical scanning devices according to the present invention is explained with respect to an optical scanning device of the embodiment 3 with magnetic force as in the embodiment 1.

Basically, a frequency of vibration in the X-direction in which a high-speed scanning by the optical fiber is performed and a frequency of vibration in the Y-direction in which a low-speed scanning by the optical fiber is performed are determined by a necessary frame rate and the number of scan lines. And, when the frequency of the vibration in the X-direction is an integer multiple of the frequency of the vibration in the Y-direction, the optical scanning device carries out the raster scan. Now, an example in which the optical scanning device of the embodiment 3 carries out the raster scan is explained below.

Figure 3A:
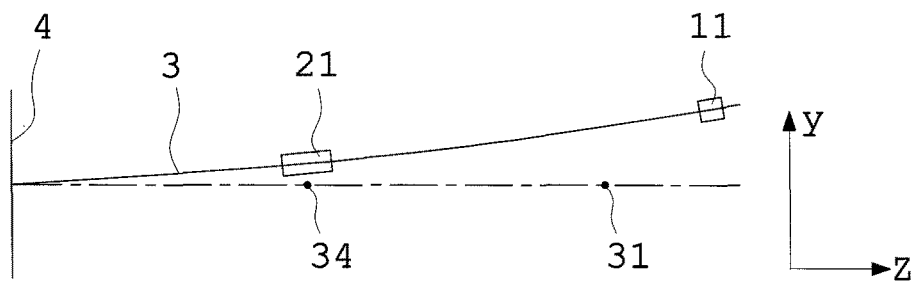
FIG. 3A is an explanatory view showing an optical scanning device according to yet another embodiment of the present invention in which the optical fiber is vibrated to resonate both in the X- and Y-directions and is a side view showing the optical scanning device when viewed in the Y-direction.
Figure 3B:
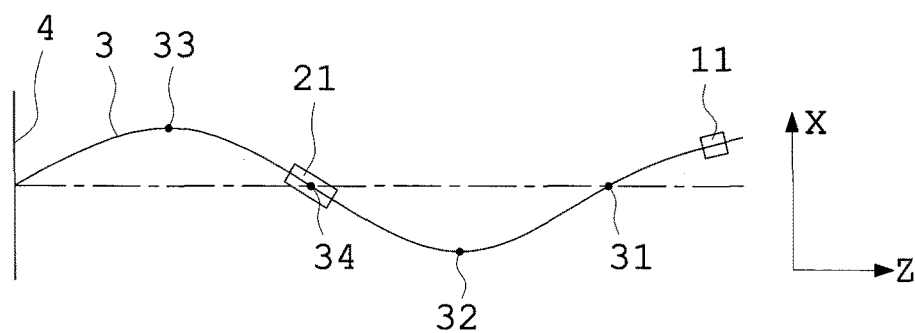
FIG. 3B is an explanatory view showing the optical scanning device according to yet another embodiment of the present invention in which the optical fiber is vibrated to resonate both in the X- and Y-directions and is a side view showing the optical scanning device when viewed in the X-direction.

FIGS. 3A and 3B show one example of the optical scanning device of the embodiment 3 in which: a third-order resonant frequency is used in the X-direction for high-speed scanning; and a first-order resonant frequency is used in the Y-direction for low-speed scanning. In the optical scanning device of the example shown in FIGS. 3A and 3B, the first-order resonant frequency for the vibration in the Y-direction is 233 Hz and the third-order resonant frequency for the vibration in the X-direction is 7600 Hz, for example. Also, in the optical scanning device of the example shown in FIGS. 3A and 3B, it is desirable that an electric signal applied to the second driving device 20 is a periodic signal like a sine wave or triangle wave so that scans in the X-direction are performed at regular intervals. Besides, the optical scanning device of the example shown in FIGS. 3A and 3B is configured to make it possible to properly select a first-order resonant frequency for vibration in the Y-direction from the range of 100 Hz to 1000 Hz.

In order that the single mode optical fiber 3 vibrates in the Y-direction and in the X-direction as shown in FIGS. 3A and 3B, the permanent magnet 11 for the first driving device 10 for the vibration in the Y-direction is arranged to be located nearer to the front end side of the optical fiber 3 than a position of a front-end-side node 31 in the vibration of the optical fiber 3. In addition, the permanent magnet 21 for the second driving device 20 for the vibration in the X-direction is preferably placed between positions of a front-end-side antinode 32 and a holding member-4-side antinode 33 in the vibration of the optical fiber 3, for example, at a position of a node 34 that is located between the antinodes 32 and 33. Alternatively, the permanent magnet 21 for the second driving device 20 may be placed at the position of the front-end-side antinode 32 as well as the position of the node 34 in the vibration of the optical fiber 3. However, if the permanent magnet 21 for the second driving device 20 is placed between the holding member 4 and the first driving device 10, there is no necessity that the permanent magnet 21 for the second driving device 20 should be located at one of the above-described positions.

Figure 4A:
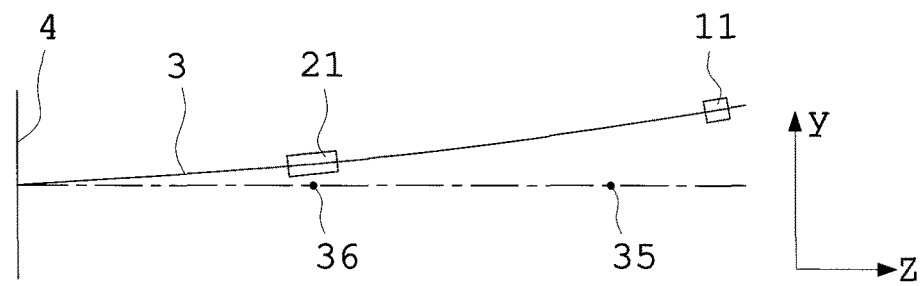
FIG. 4A is an explanatory view showing an optical scanning device according to yet another embodiment of the present invention in which the optical fiber is vibrated in the X-direction to resonate and is vibrated in the Y-direction without being made to resonate and is a side view showing the optical scanning device when viewed in the Y-direction.
Figure 4B:
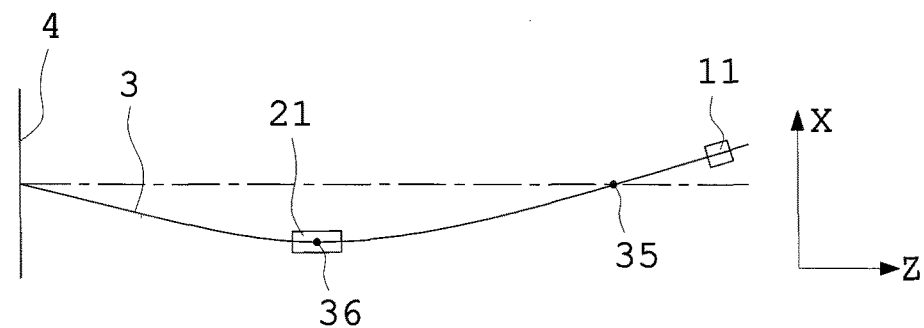
FIG. 4B is an explanatory view showing the optical scanning device according to yet another embodiment of the present invention in which the optical fiber is vibrated in the X-direction to resonate and is vibrated in the Y-direction without being made to resonate and is a side view showing the optical scanning device when viewed in the X-direction.
Figure 5:
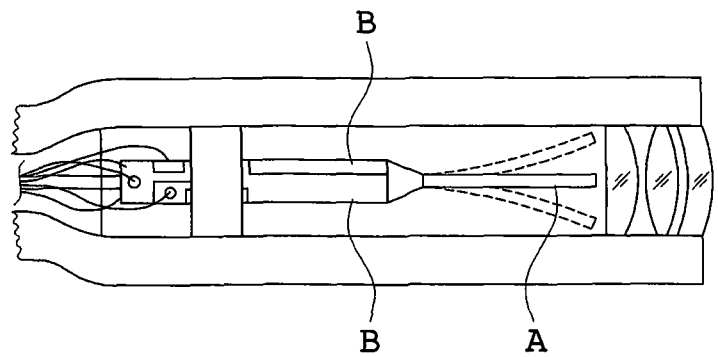
FIG. 5 is an explanatory view showing an example of conventional optical scanning devices in the prior art.
Figure 6A:
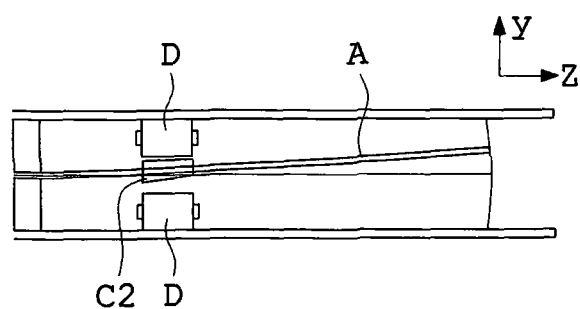
FIGS. 6A-6B are explanatory views showing another example of conventional optical scanning devices in the prior art.
Figure 6B:
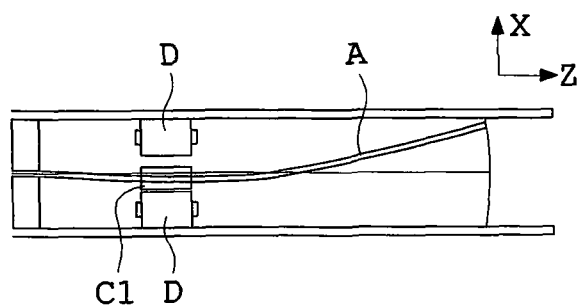
Figure 7:
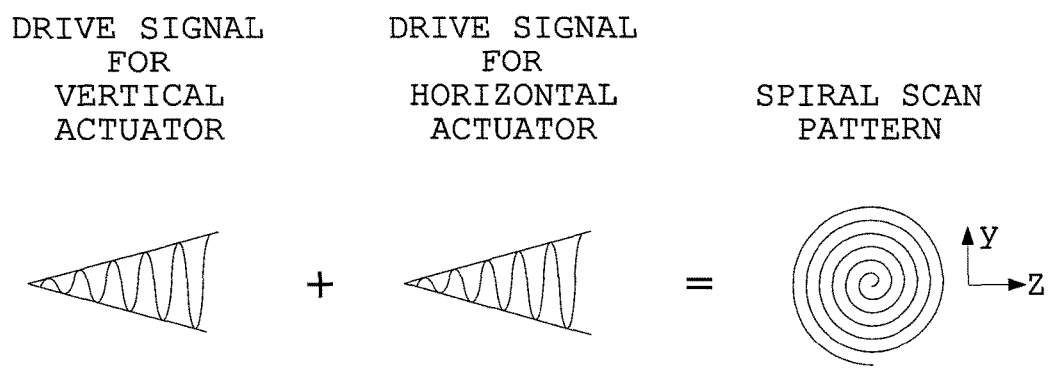
FIG. 7 is an explanatory view explaining a spiral scan.
Figure 8:
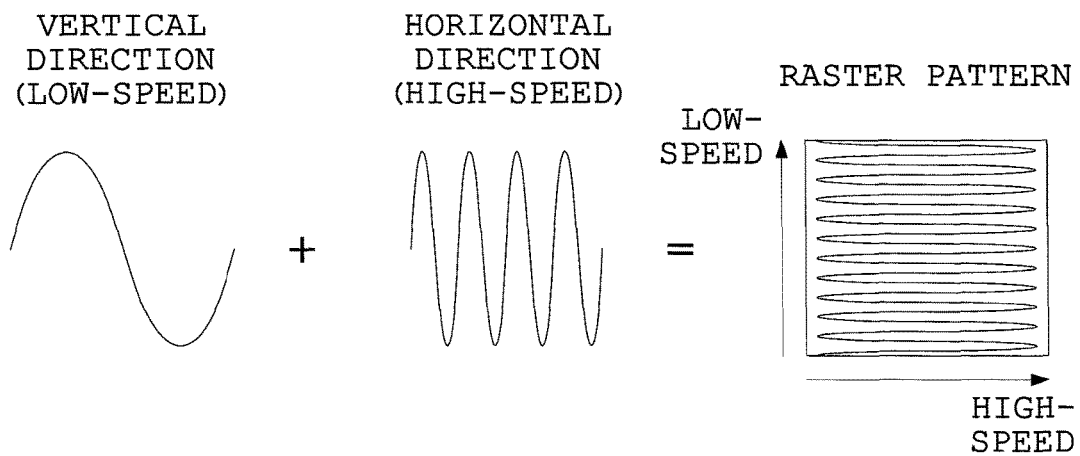
FIG. 8 is an explanatory view explaining a raster scan.

FIGS. 4A and 4B show another example of the optical scanning device of the embodiment 3 in which: the second-order resonant frequency is used in the X-direction for high-speed scanning; and a non-resonant frequency lower than the first-order resonant frequency is used in the Y-direction for low-speed scanning. In the optical scanning device of the example shown in FIGS. 4A and 4B, it is desirable that an electric signal applied to the second driving device 20 is a periodic signal like a sine wave or triangle wave so that scans in the X-direction are performed at regular intervals. Besides, the example of optical scanning devices shown in FIGS. 4A and 4B is configured to make it possible to properly select a non-resonant frequency for vibration in the Y-direction from the range of 1 Hz to 1000 Hz.

In order that the optical fiber 3 vibrates in the Y-direction and in the X-direction as shown in FIGS. 4A and 4B, the permanent magnet 11 for the first driving device 10 for the vibration in the Y-direction is arranged to be located nearer to the front-end side of the optical fiber 3 than a position of a node 35 in the vibration of the optical fiber 3. In addition, the permanent magnet 21 for the second driving device 20 for the vibration in the X-direction is preferably placed between the position of the node 35 in the vibration of the optical fiber 3 and the holding member 4, for example, at a position of an antinode 36. However, if the permanent magnet 21 for the second driving device 20 is placed between the holding member 4 and the first driving device 10, there is no necessity that the permanent magnet 21 for the second driving device 20 should be located at one of the above-described positions.

According to the optical scanning device of the present embodiment, when an electric signal applied to the second driving device 20 is a periodic signal like a sine wave or a triangle wave, scan lines are evenly spaced in the Y-direction in the case where scanning in the X-direction is performed at high speed in a raster scan.

Embodiment 4

An optical scanning endoscope, an optical scanning microscope, and an optical scanning projector in the embodiment 4 each of which is provided with optical scanning device are those including optical scanning devices according to the present invention as described above instead of conventional optical scanning devices used for these apparatuses in the prior art. As a result, these apparatuses provided with optical scanning devices according to the present invention respectively become an endoscope, a microscope, and a projector each of which has effects of the optical scanning devices according to the present invention.

In the above-described embodiment, the optical fiber 3 may be an optional light-guiding member the core of which is configured as a single mode. Optical fibers each including a core of single mode are suitable for effectively combining respective vibrations by the first and second driving devices 10 and 20 into a desired scanning pattern.

Optical scanning devices according to the present invention are not limited to applications to endoscopes, microscopes, and projectors, and can be used for various kinds of apparatuses which use optical scanning devices to perform raster scan or Lissajous scan.

What is claimed is:

1. An optical scanning device comprising
   an optical fiber,
   a holding member cantilevering the optical fiber,
   a first driving device placed on a distal end of the optical fiber and making the optical fiber vibrate in a first direction, and
   a second driving device placed between the holding member for the optical fiber and the first driving device and making the optical fiber vibrate in a second direction which crosses the first direction;
   wherein the first direction in which the optical fiber is made to vibrate by the first driving device is perpendicular to the second direction which crosses the first direction and in which the optical fiber is made to vibrate by the second driving device; and
   the optical fiber is made to vibrate in a first-order vibration mode by the first driving device-and the optical fiber is made to vibrate in a second or third-order vibration mode by the second driving device.

2. The optical scanning device according to claim 1, wherein the first driving device makes the optical fiber resonate to vibrate.

3. The optical scanning device according to claim 1, wherein the first driving device makes the optical fiber vibrate without resonance.

4. The optical scanning device according to claim 1, wherein the second driving device makes the optical fiber resonate to vibrate.

5. The optical scanning device according to claim 1, wherein each of at least one of the first driving device and the second driving device comprises a magnet or magnetic substance, and an electromagnetic coil.

6. The optical scanning device according to claim 5, wherein an electric signal applied to the second driving device is a periodic signal such as sine wave or triangle wave.

7. The optical scanning device according to claim 1, wherein each of at least one of the first driving device and the second driving device comprises a piezoelectric device formed into a thin film provided for the optical fiber.

8. An endoscope comprising the optical scanning device according to claim 1.

9. A microscope comprising the optical scanning device according to claim 1.

10. A projector comprising the optical scanning device according to claim 1.

11. A method of driving an optical fiber provided for an optical scanning device and cantilevered by a holding member, comprising
    making the optical fiber vibrate in a first direction by a first driving device placed on a distal end of the optical fiber, and
    making the optical fiber vibrate in a second direction by a second driving device placed between the holding member for the optical fiber and the first driving device, the second direction crossing the first direction;

wherein the first direction in which the optical fiber is made to vibrate by the first driving device is perpendicular to the second direction in which the optical fiber is made to vibrate by the second driving device; and the optical fiber is made to vibrate in a first-order vibration mode by the first driving device and the optical fiber is made to vibrate in a second or third-order vibration mode by the second driving device.

12. The method of driving an optical fiber according to claim 11, wherein the optical fiber is made to resonate to vibrate by the first driving device.

13. The method of driving an optical fiber according to claim 11, wherein the optical fiber is made to vibrate without resonance by the first driving device.

14. The method of driving an optical fiber according to claim 11, wherein the optical fiber is made to resonate to vibrate by the second driving device.

15. The method of driving an optical fiber according to claim 11, wherein an electric signal which is a periodic signal such as sine wave or triangle wave is applied to the second driving device.

\* \* \* \* \*